United States Patent
Komuro

(10) Patent No.: US 11,553,975 B2
(45) Date of Patent: Jan. 17, 2023

(54) MEDICAL MANIPULATOR SYSTEM AND METHOD FOR OPERATING SAME

(71) Applicant: OLYMPUS CORPORATION, Hachioji (JP)

(72) Inventor: Takahiro Komuro, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 430 days.

(21) Appl. No.: 16/849,068

(22) Filed: Apr. 15, 2020

(65) Prior Publication Data
US 2020/0237469 A1  Jul. 30, 2020

Related U.S. Application Data

(63) Continuation of application No. PCT/JP2017/040537, filed on Nov. 10, 2017.

(51) Int. Cl.
*A61B 34/00* (2016.01)
*A61B 34/20* (2016.01)
*A61B 90/00* (2016.01)
*A61B 1/00* (2006.01)
*A61B 17/00* (2006.01)

(52) U.S. Cl.
CPC .............. *A61B 34/74* (2016.02); *A61B 34/71* (2016.02); *A61B 1/00154* (2013.01); *A61B 2017/00725* (2013.01); *A61B 2034/2059* (2016.02); *A61B 2034/256* (2016.02); *A61B 2090/067* (2016.02)

(58) Field of Classification Search
CPC . A61B 1/00154; A61B 1/0016; A61B 1/0051; A61B 2017/00017; A61B 2017/00725; A61B 2018/00988; A61B 2034/2059; A61B 2034/256;
(Continued)

(56) References Cited

U.S. PATENT DOCUMENTS 8,428,779 B2   4/2013  Ohga et al.
2009/0259340 A1  10/2009  Umemoto et al.
(Continued)

FOREIGN PATENT DOCUMENTS

EP  2110212 A2  10/2009
EP  3025632 A1   6/2016
(Continued)

OTHER PUBLICATIONS

Jan. 30, 2018 International Search Report issued in International Application No. PCT/JP2017/040537.

*Primary Examiner* — Michael T Rozanski
(74) *Attorney, Agent, or Firm* — Oliff PLC

(57) ABSTRACT

A medical manipulator system that includes a joint, a first sensor that detects an amount of rotational motion of the joint, an actuator that drives the joint via a wire, a second sensor that detects an amount of operation of the actuator based on a rotation angle of the actuator, an input device, and a controller. The controller generates a control signal based on: an operation mode in which the control signal is generated by a transfer function that receives an input target value of the rotation angle of the joint and the amount of operation of the actuator, and a calibration mode in which the transfer function is adjusted based on comparing to a predetermined threshold value the amount of rotational motion of the joint and the amount of operation of the actuator. The controller then transmits the generated control signal to the actuator to drive the joint.

6 Claims, 13 Drawing Sheets

(58) Field of Classification Search
CPC ... A61B 2090/067; A61B 34/30; A61B 34/71;
A61B 34/74
See application file for complete search history.

(56) References Cited

U.S. PATENT DOCUMENTS

| | | |
|---|---|---|
| 2012/0150347 A1 | 6/2012 | Ohga et al. |
| 2014/0107667 A1 | 4/2014 | Komuro et al. |
| 2016/0136810 A1 | 5/2016 | Wakai et al. |
| 2016/0361819 A1 | 12/2016 | Wakai et al. |

FOREIGN PATENT DOCUMENTS

| | | |
|---|---|---|
| EP | 3147085 A1 | 3/2017 |
| JP | 2002-264048 A | 9/2002 |
| JP | 2006-055927 A | 3/2006 |
| JP | 2009-254519 A | 11/2009 |
| JP | 2013-031637 A | 2/2013 |
| JP | 2015-023950 A | 2/2015 |
| JP | 2015-163413 A | 9/2015 |
| WO | 2011-036750 A1 | 3/2011 |
| WO | 2013-002414 A1 | 1/2013 |
| WO | 2015-129607 A1 | 9/2015 |

FIG. 8

TREATMENT TOOL P1

| ANGLE DIFFERENCE $\Delta 1$ | ke | RECIPROCATING ANGLE DIFFERENCE $\Delta 2$ | kd |
|---|---|---|---|
| $1 \leqq \Delta 1 < 2$ | 3200 | $1 \leqq \Delta 1 < 2$ | 1000 |
| $2 \leqq \Delta 1 < 4$ | 3050 | $2 \leqq \Delta 1 < 4$ | 1100 |
| . | . | . | . |
| . | . | . | . |
| . | . | . | . |

MEDICAL MANIPULATOR SYSTEM AND METHOD FOR OPERATING SAME

CROSS-REFERENCE TO RELATED APPLICATION

This is a continuation of International Application No. PCT/JP2017/040537, which is hereby incorporated by reference herein in its entirety.

TECHNICAL FIELD

The present embodiments relate to a medical manipulator system and a method for operating the same.

BACKGROUND

There are well-known medical manipulator systems in which a joint provided at the distal end of an elongated insertion section is moved by pulling a wire by means of a motor provided at the proximal end of the insertion section.

In order to prevent a discrepancy between the amount of operation and the amount of curvature due to looseness and friction of the wire, such a medical manipulator system has a sensor mounted in the vicinity of the joint at the distal end of the insertion section to detect the amount of movement of the wire by means of the sensor and an encoder mounted in the motor for pulling the wire, thereby feedback-controlling the motor in a real-time manner on the basis of signals detected by both the sensor and the encoder.

SUMMARY

One aspect is a medical manipulator system including an elongated insertion section including a joint at a distal end portion of the insertion section; a first sensor configured to detect an amount of rotational motion of the joint of the insertion section; an actuator disposed at a proximal end of the insertion section, the actuator being configured to drive the joint via a wire connected to the joint; a second sensor configured to detect an amount of operation of the actuator based on a rotation angle of the actuator; an input device operated by a user; and a controller configured to: generate a control signal based on: an operation mode in which the control signal is generated by a transfer function that receives, as inputs, an input target value of a rotation angle of the joint that is input on the input device and the amount of operation of the actuator detected by the second sensor, and a calibration mode in which the transfer function is adjusted based on comparing to a predetermined threshold value (i) the amount of rotational motion of the joint detected by the first sensor and (ii) the amount of operation of the actuator detected by the second sensor; and transmit the generated control signal to the actuator to drive the joint based on the generated control signal.

Another aspect is a method for operating a medical manipulator system that includes a first sensor configured to detect an amount of rotational motion of a joint provided at a distal end portion of an elongated insertion section, a second sensor configured to detect an amount of operation of an actuator based on a rotation angle of the joint disposed at a proximal end of the insertion section and drive the joint via a wire connected to the joint, and an input device operated by a user, the method including: setting control gains of a transfer function to initial values, the transfer function receiving, as inputs, an input target value of a rotation angle of the joint that is input on the input device and the amount of operation of the actuator detected by the second sensor; moving the joint with a predetermined pattern; calculating a difference between the amount of rotational motion of the joint detected by the first sensor and the amount of operation of the actuator detected by the second sensor; determining whether the calculated difference is equal to or less than a predetermined threshold value; in response to determining that the calculated difference is not equal to or less than the predetermined threshold value, updating the control gains of the transfer function; and generating and transmitting a control signal based on the transfer function to the actuator to drive the joint based on the generated control signal.

BRIEF DESCRIPTION OF DRAWINGS

FIG. 8 is a diagram depicting one example of a table stored in a memory of the medical manipulator system in FIG. 7.

DESCRIPTION OF EMBODIMENTS

A medical manipulator system 1 and a method for operating the same according to one embodiment will now be described with reference to the drawings.

Figure 1:
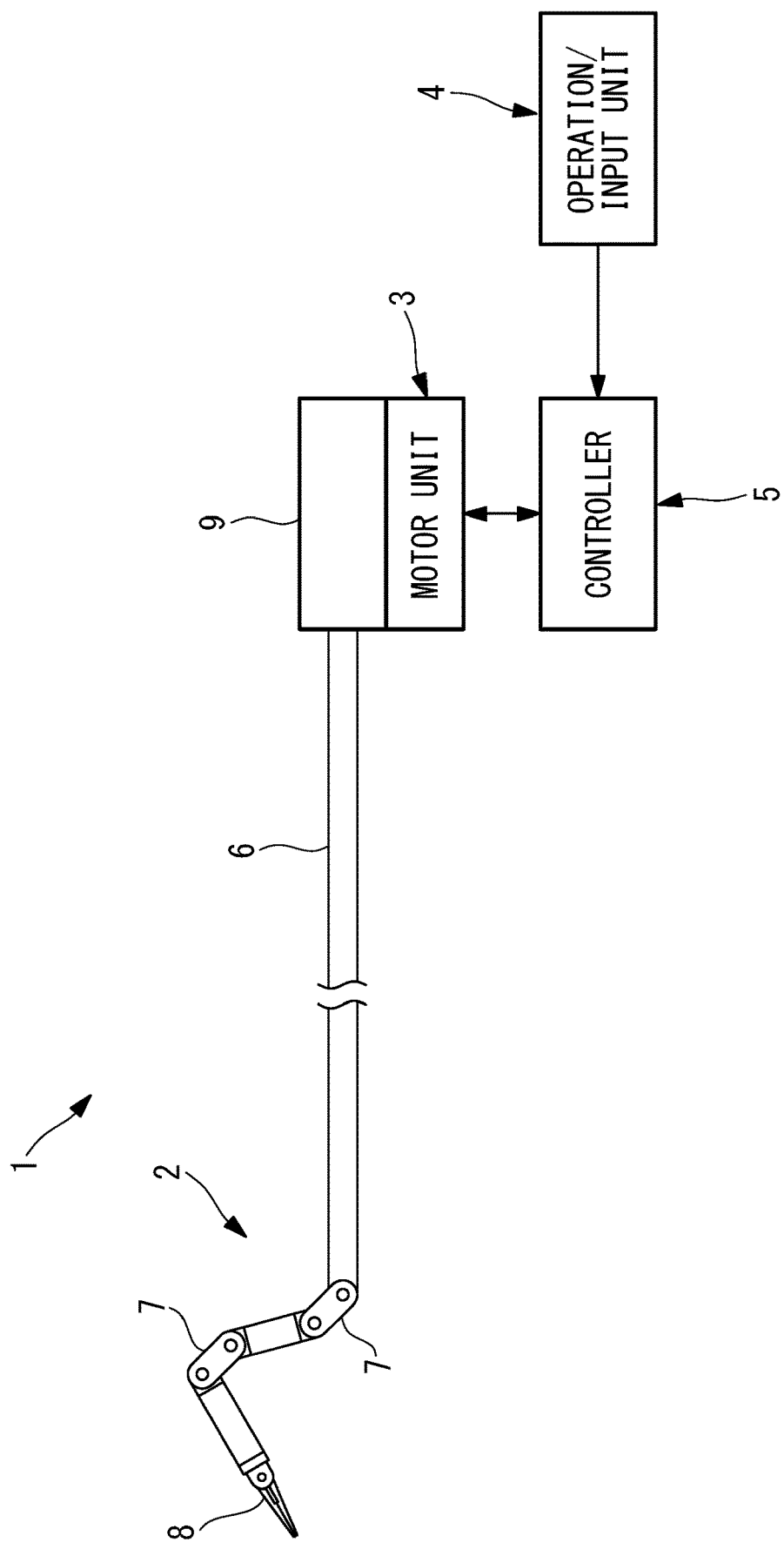
FIG. 1 is an overall configuration diagram showing a medical manipulator system according to one embodiment.
Figure 2:
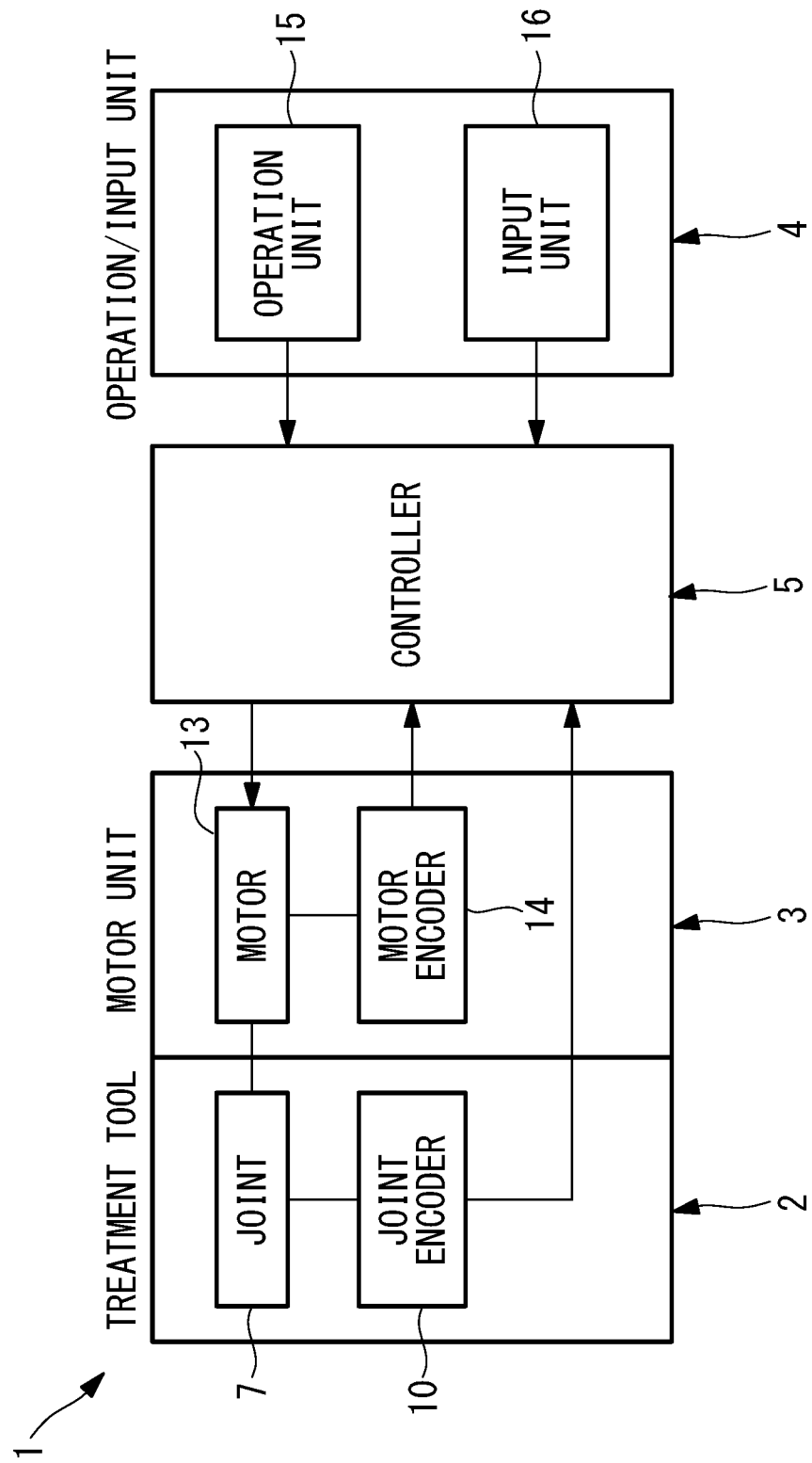
FIG. 2 is a block diagram showing the medical manipulator system in FIG. 1.
Figure 3:
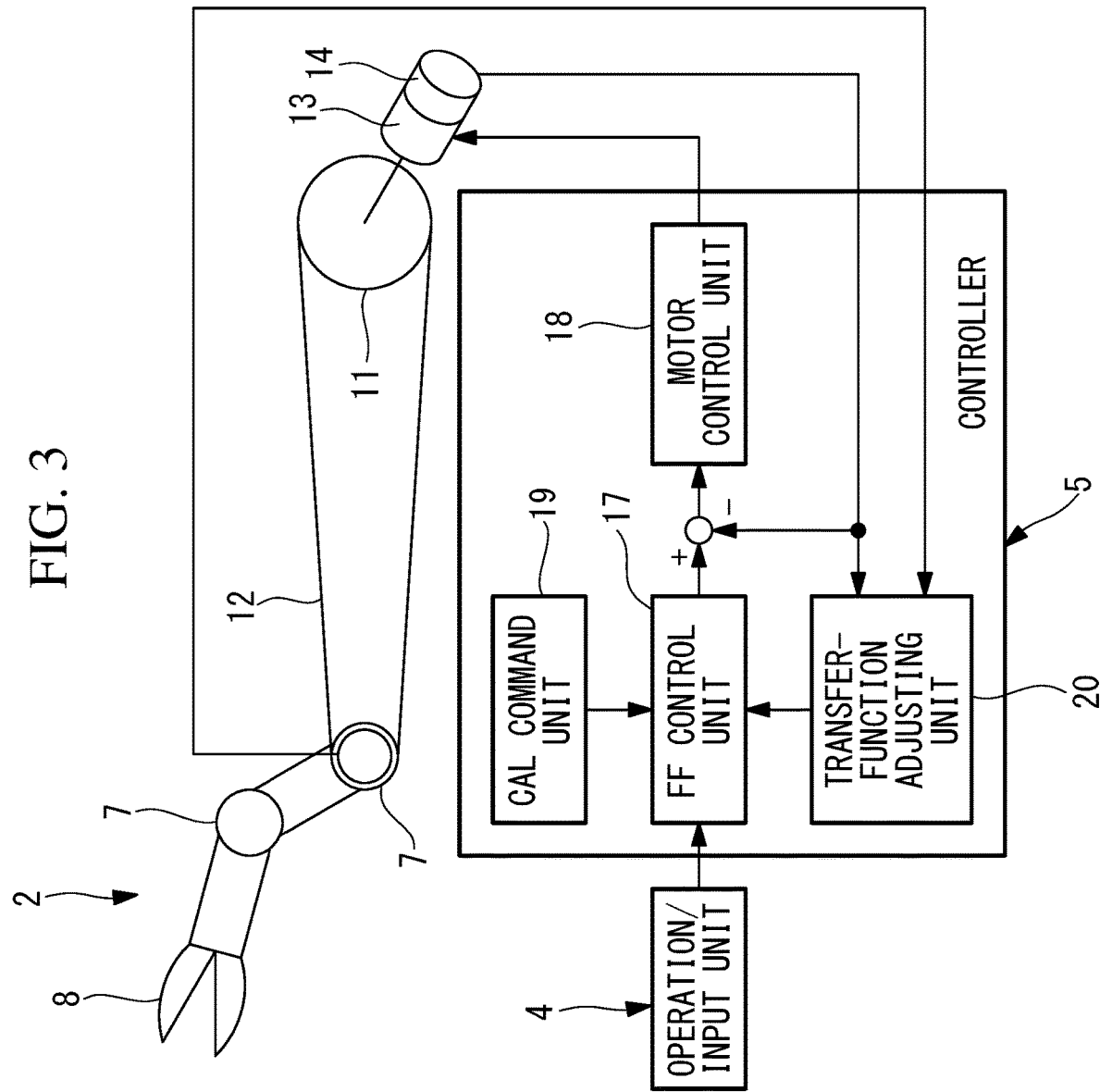
FIG. 3 is a block diagram for illustrating a controller included in the medical manipulator system in FIG. 2.

As shown in FIGS. 1 to 3, the medical manipulator system 1 according to this embodiment includes, a treatment tool 2 for treating an affected area, a motor unit 3 for driving the treatment tool 2, an operation/input unit 4 for allowing a user to perform inputs and operations, and a controller 5 for controlling the motor unit 3 in accordance with the user's operations performed with the operation/input unit 4.

The treatment tool 2 includes joints 7 at the distal end portion of an elongated insertion section 6 and includes a treatment section 8 at the distal end of a joint 7. In addition, the treatment tool 2 includes, at the proximal end of the insertion section 6, a connecting section 9 that is connected to the motor unit 3. Each of the joints 7 includes a joint encoder (first sensor) 10 for detecting the swivel angle (the amount of motion) of the joint 7. A pulley 11 to which a motor 13 (described below) is detachably connected is disposed in the connecting section 9. A joint 7 and the pulley 11 are connected with a wire 12 that is wound and hung on the pulley 11, so that the joint 7 can be rotationally driven by transmitting the rotation of the pulley 11 via the wire 12.

The motor unit 3 includes the motor (actuator) 13, and a motor encoder (second sensor) 14 that is connected to the motor 13 and that detects the rotation angle of the motor 13.

The operation/input unit 4 includes an operation unit 15, such as a handle that is gripped and moved by the user with a single hand or both hands, and an input unit 16 used to input a command for instructing the start of an operation (operation mode) or the release of the operation, a command for instructing the start of a calibration (calibration mode), etc.

The controller 5 includes an arithmetic processing unit (processor) and a memory, which are not shown in the figures. When a command for instructing the start of an operation is input on the input unit 16 in the operation mode, the arithmetic processing unit calculates an operating command signal to be sent to the motor 13 on the basis of the target angle of a joint 7 instructed with the operation unit 15 and the rotation angle of the motor 13 fed back from the motor encoder 14 and outputs the operating command signal. A calibration program is stored in the memory.

FIG. 3 shows a control block diagram for the motor 13 with the arithmetic processing unit.

The arithmetic processing unit includes a feedforward control unit (FF control unit) 17, and a motor control unit 18 for generating a drive command for driving the motor 13. When a target angle (input value) is input with the operation/input unit 4, the deviation between an angle command resulting from the input target angle being adjusted by a transfer function of the feedforward control unit 17 and the rotation angle of the motor 13 fed back from the motor encoder 14 is input to the motor control unit 18, and a drive command for driving the motor 13 is then generated and input to the motor 13. At this time, information on the swivel angle of the joint 7 coming from the joint encoder 10 is not used.

In addition, the arithmetic processing unit includes a CAL command unit 19 that, when a command for instructing the release of an operation is input and a command for instructing the start of a calibration is input on the input unit 16, reads out and executes the calibration program stored in the memory, thereby outputting a target angle for moving the joint 7 with a predetermined pattern. The arithmetic processing unit also includes a transfer-function adjusting unit 20 for calculating control gains of the transfer function.

When the calibration program is executed and a target angle is output from the CAL command unit 19, the joint 7 is moved, and the rotation angle of the motor 13 detected by the motor encoder 14 at that time and the swivel angle of the joint 7 detected by the joint encoder 10 are input to the transfer-function adjusting unit 20. In the transfer-function adjusting unit 20, the control gains of the transfer function of the FF control unit 17 are calculated on the basis of the rotation angle of the motor 13 and the swivel angle of the joint 7 and are then input to the FF control unit 17.

The transfer function of the FF control unit 17 includes a control gain kd for compensating for looseness of the wire 12, and a control gain ke for compensating for an attenuation of the displacement angle of the joint 7 based on the shape, etc. of the insertion section 6.

Figure 4:
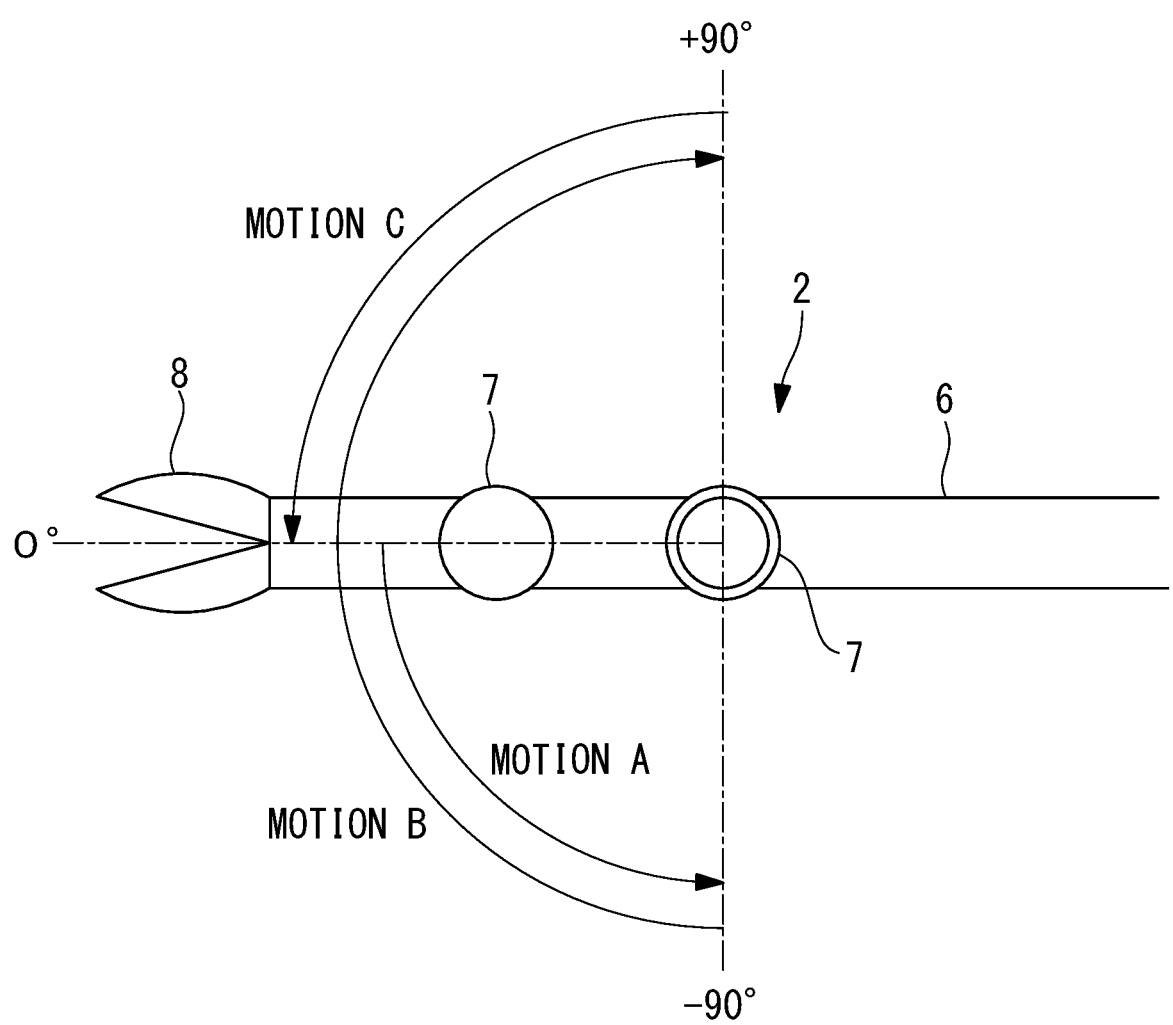
FIG. 4 is a diagram depicting one example of calibration motions in the medical manipulator system in FIG. 1.

As shown in, for example, FIG. 4, the calibration program includes a motion A for moving each of the joints 7 from 0° to −90°, a motion B for moving each of the joints 7 from −90° to +90°, and a motion C for moving each of the joints 7 from +90° to 0°.

The transfer-function adjusting unit 20 outputs the control gains kd and ke to the FF control unit 17 and, when each of the motions A, B, and C is performed once in that order, calculates the difference between the swivel angle of the joint 7 detected by the joint encoder 10 and an estimation angle of the joint 7 that is estimated on the basis of the rotation angle of the motor 13 detected by the motor encoder 14.

Then, the transfer-function adjusting unit 20 repeats changing the control gains kd and ke by a prescribed value (e.g., 0.1) at a time and outputting the control gains kd and ke to the FF control unit 17 until the above-described difference becomes equal to or smaller than a predetermined threshold value. By doing so, a transfer function including the control gains kd and ke that cause the above-described difference to become equal to or smaller than the predetermined threshold value is set in the FF control unit 17.

More specifically, once the adjusted transfer function has been set, switching to the operation mode allows a target angle command entered with the operation/input unit 4 to be adjusted by the set transfer function in the FF control unit 17 and to be input to the motor control unit 18, thus driving the motor 13.

Figure 5:
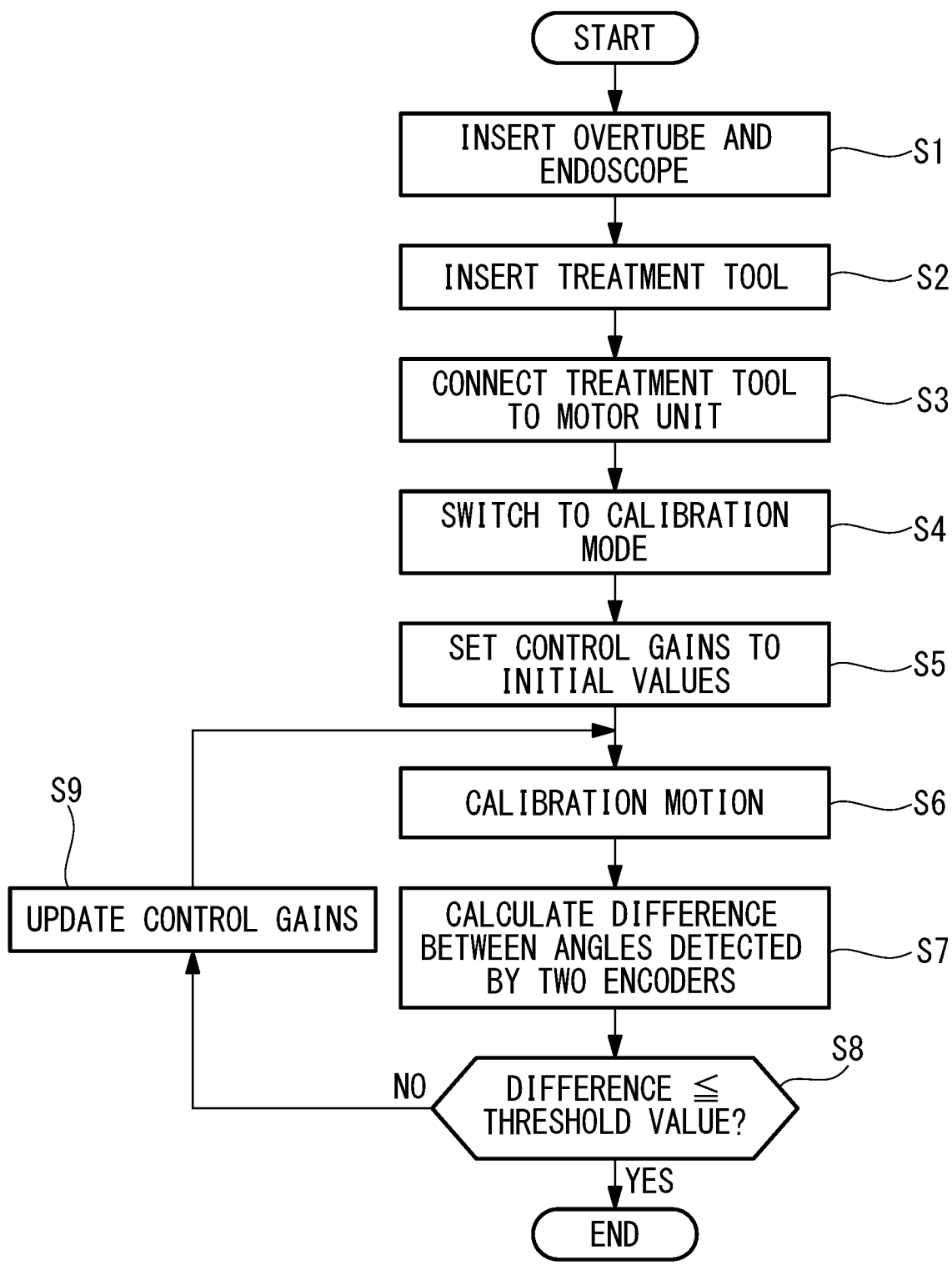
FIG. 5 is a flowchart for illustrating a calibration procedure in the medical manipulator system in FIG. 1.

The operation of the medical manipulator system 1 according to this embodiment with the above-described configuration will be described with reference to the flowchart in FIG. 5. In order to use the medical manipulator system 1 according to this embodiment, first the user inserts, into the body of a patient, an overtube and an endoscope disposed in the overtube along body cavity of the patient (step S1). When an affected area to be treated appears in the field of view of the endoscope, the form of the endoscope is determined.

Next, the user inserts the treatment tool 2 into the body of the patient through a channel provided in the overtube (step S2). By doing so, the form of the treatment tool 2 is determined. Then, the connecting section 9 provided at the proximal end of the insertion section 6 of the treatment tool 2 is connected to the motor unit 3 outside the patient body (step S3).

In this state, when the user performs an input for switching to the calibration mode on the input unit of the operation/input unit 4 (step S4), the control gains kd and ke of the transfer function of the FF control unit 17 are set to initial values (step S5), the calibration program read out by the CAL command unit 19 from the memory is executed in the arithmetic processing unit, and the joint 7 is moved with the predetermined pattern (step S6).

Then, subsequent to this motion, the difference between the swivel angle of the joint 7 detected by the joint encoder 10 and the estimation angle of the joint 7 based on the rotation angle of the motor 13 detected by the motor encoder 14 is calculated (step S7), and it is determined whether or not the difference is equal to or smaller than the predetermined threshold value (step S8). In the case where the difference exceeds the predetermined threshold value, the control gains kd and ke are updated (step S9), and the steps from step S6 on are repeated. In the case where the difference is equal to or smaller than the predetermined threshold value, the calibration mode ends.

Thereafter, as a result of the user switching to the operation mode on the input unit 16, the user can move the joint 7 by operating the operation unit 15. In this manner, it is possible to stably move the joint 7 according to the operations and inputs because the attenuation of the angle displacement depending on backlash, friction, and the form of the insertion section 6 is compensated for.

As described above, according to the medical manipulator system 1 of this embodiment, it is possible to feedback-control the motor 13 with high accuracy by using a relatively high-resolution encoder as the motor encoder 14. In addition, as a result of the transfer function of the FF control unit 17 being properly adjusted, the joint 7 at the distal end portion of the insertion section 6 can be controlled according to the operations and inputs, irrespective of looseness and friction of the wire 12.

Figure 6:
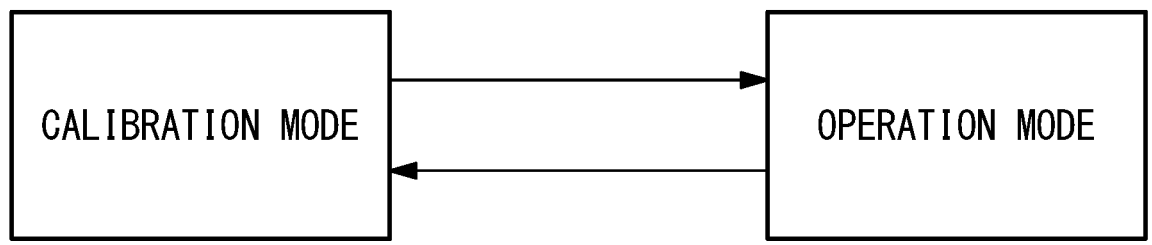
FIG. 6 is a diagram showing a mode transition in the medical manipulator system in FIG. 1.

Furthermore, according to the medical manipulator system 1 of this embodiment, information on the swivel angle of the joint 7 detected by the joint encoder 10 is used only when the transfer function of the FF control unit 17 is adjusted in the calibration mode. Thus, because information on the swivel angle of the joint 7 detected by the joint encoder 10 is not used in a real-time manner when the joint 7 is moved in the operation mode (the operation mode and the calibration mode are switched to each other as shown in FIG. 6), the medical manipulator system 1 according to this embodiment affords an advantage in that the joint 7 can be stably moved even when a low-resolution encoder is used as the joint encoder 10. In addition, because a low-resolution, compact encoder can be used as the joint encoder 10 disposed at the distal end portion of the insertion section 6, the medical manipulator system 1 according to this embodiment also affords an advantage in that the diameter of the distal end portion of the insertion section 6 can be reduced.

Figure 7:
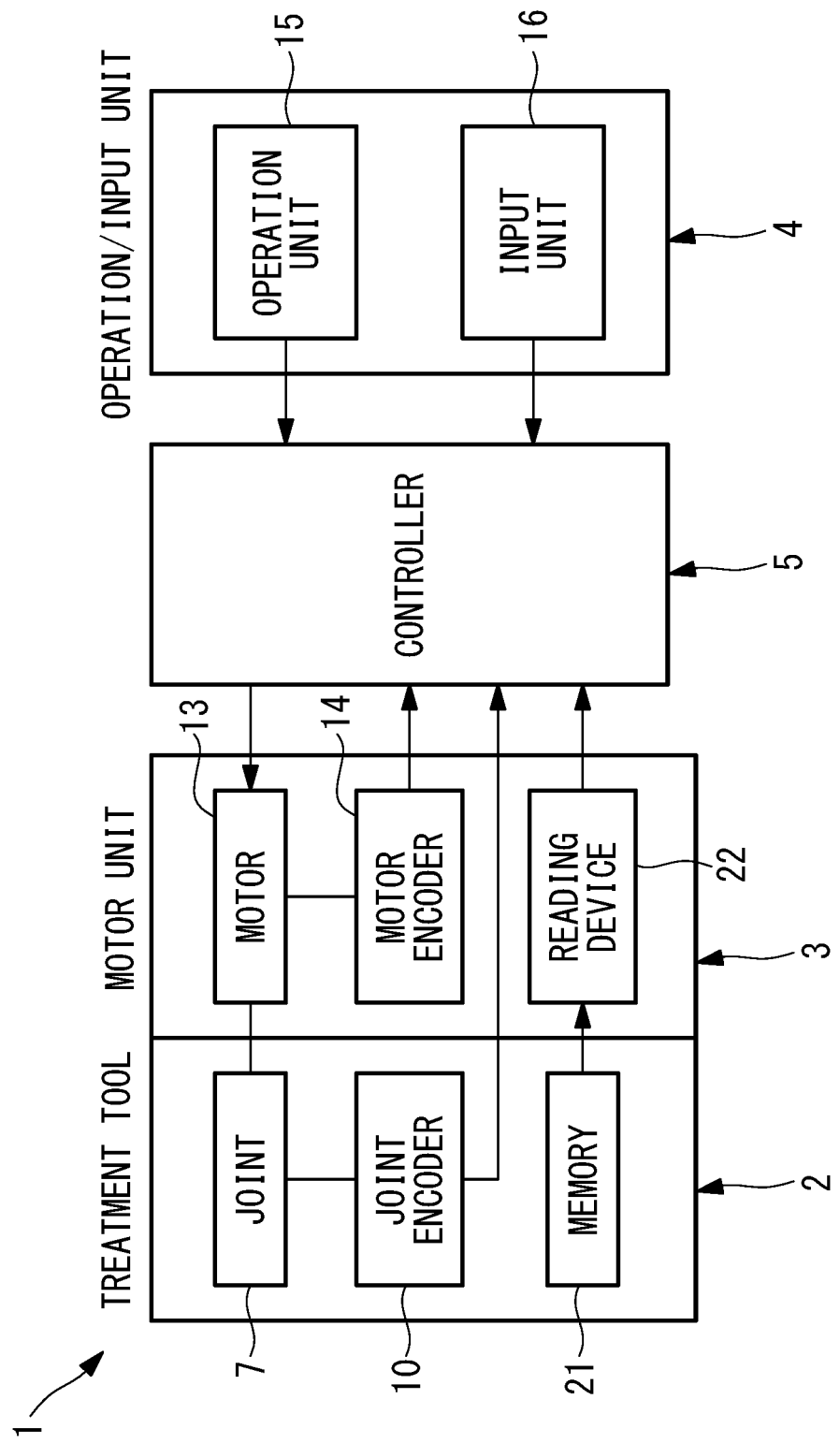
FIG. 7 is a block diagram showing a modification of the medical manipulator system in FIG. 1.

Note that although this embodiment has been described by way of an example where the control gains kd and ke are converged by repeating calibration motions until the swivel angle detected by the joint encoder 10 substantially coincides with the estimation angle of the joint 7 based on the rotation angle detected by the motor encoder 14, instead of this, as shown in FIG. 7, the treatment tool 2 may include a memory 21 for storing identification information for identifying the treatment tool 2, the motor unit 3 may include a reading device 22 for reading out the identification information in the memory 21 when the connecting section 9 of the treatment tool 2 is connected thereto, and the memory of the controller 5 may include a table that stores desired control gains kd and ke for each item of identification information of the treatment tool 2 in association with differences Δ1, Δ2 between the swivel angle of the joint 7, which is detected by the joint encoder 10 when calibration motions are performed with standard control gains kd and ke, and the estimation angle based on the motor encoder 14.

FIG. 8 shows one example of such a table. The difference Δ1 is the difference when, for example, each of the motion A, the motion B, and the motion C in FIG. 4 is carried out independently, and the difference (reciprocating difference) Δ2 is the difference when, for example, the round-trip motions A and B or the round-trip motions B and C in FIG. 4 are carried out successively.

Figure 9:
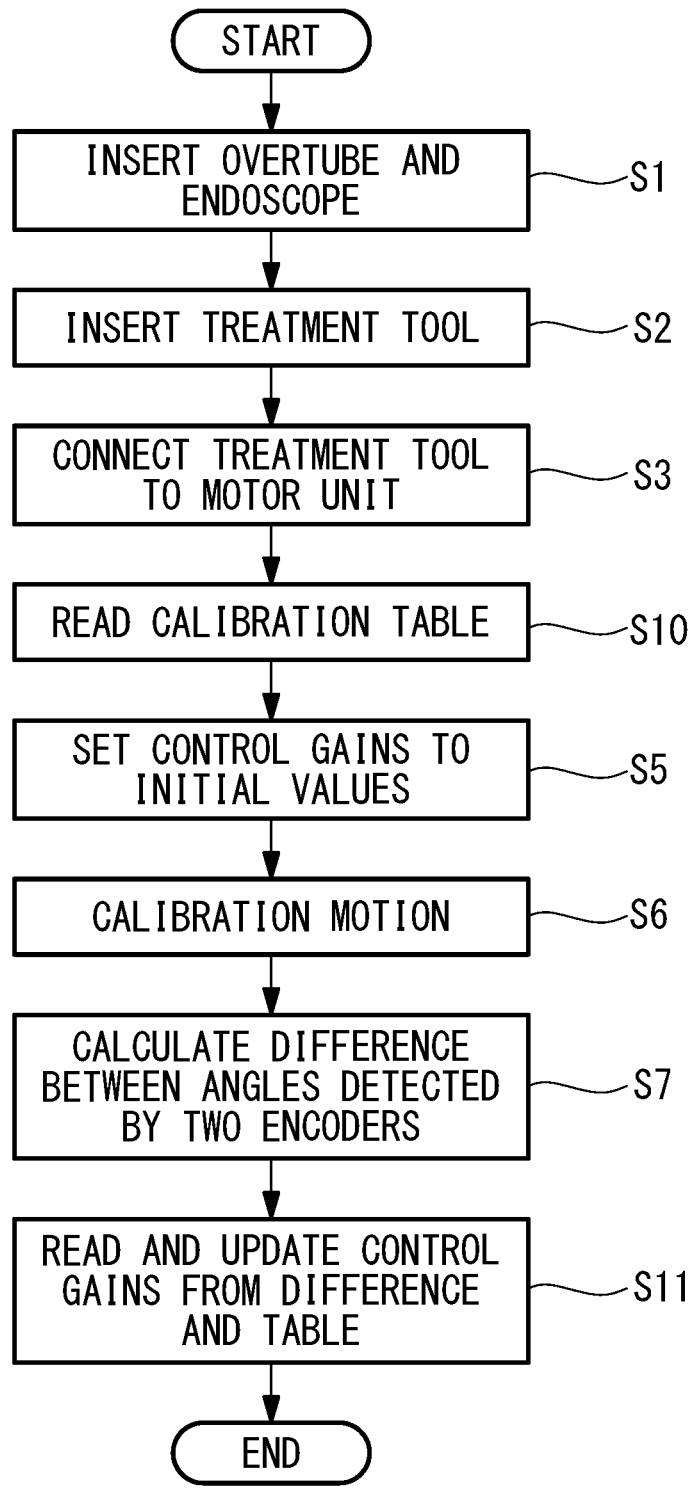
FIG. 9 is a flowchart for illustrating a calibration procedure in the medical manipulator system in FIG. 7.

Also, as shown in FIG. 9, this embodiment affords an advantage in that desired control gains kd and ke can be obtained from the table merely by setting standard control gains kd and ke as the initial values of the control gains kd and ke in step S5, performing a single operation of each of the calibration motions A, B, and C and the calculation of a difference as described above, and searching the table for the control gains kd and ke corresponding to the calculated difference.

In other words, merely by connecting the treatment tool 2 to the motor unit 3 in step S3, reading out the calibration table (step S10), and then carrying out calibration motions once, it is possible to read out and update the control gains kd and ke from a difference, in the table, between the angles detected by the two respective encoders 10 and 14 (step S11).

In addition, although this embodiment has been described by way of an example where the joint 7 is moved in the order of 0° to −90°, −90° to +90°, and +90° to 0° for the calibration motions, instead of this, the calibration motions may be performed to cover the entire movable range of the joint 7 or may be performed to cover a range smaller than the movable range. In addition, although this embodiment has been described by way of an example where the calibration motions are performed in both positive and negative directions with respect to 0°, the calibration motions may be performed only in one direction.

Furthermore, although this embodiment has been described by way of an example where the difference between the angles detected by the two encoders 10 and 14 is calculated for each of the calibration motions in which the joint 7 is moved in the order of 0° to −90°, −90° to +90°, and +90° to 0°, instead of this, the control gain ke may be calculated by moving the joint 7 by a prescribed angular range, e.g., 10°, at a time, calculating the proportion of the angles for each of the angular ranges, and then calculating the average value of the proportions.

Alternatively, the joint 7 may be made to perform a reciprocating motion in a prescribed angular range (e.g., 10°), and the difference Δ2−Δ1 may be calculated, where Δ1 is the difference between the rotation angle of the motor 13 detected by the motor encoder 14 and the swivel angle of the joint 7 detected by the joint encoder 10 in the forward path, and Δ2 is the difference between the rotation angle of the motor 13 detected by the motor encoder 14 and the swivel angle of the joint 7 detected by the joint encoder 10 in the return path, thus calculating the control gain kd for each angular range.

Furthermore, in this embodiment, the calibration motions may be performed such that the joint 7 is moved within a range corresponding to the minimum unit angle (e.g., 10°) of the resolution of the joint encoder 10. In this case, the ratio between the angle of the joint 7 that is detected first by the joint encoder 10 and the angle of the joint 7 that is estimated on the basis of the angle detected by the motor encoder 14 can be used as-is for the control gains kd and ke. Alternatively, the table may be searched for the control gains kd and ke corresponding to the above-described ratio. By doing so, the transfer function of the FF control unit 17 can be adjusted properly even in the case where the treatment tool 2 cannot be moved by a large amount in the narrow body cavity.

Figure 10:
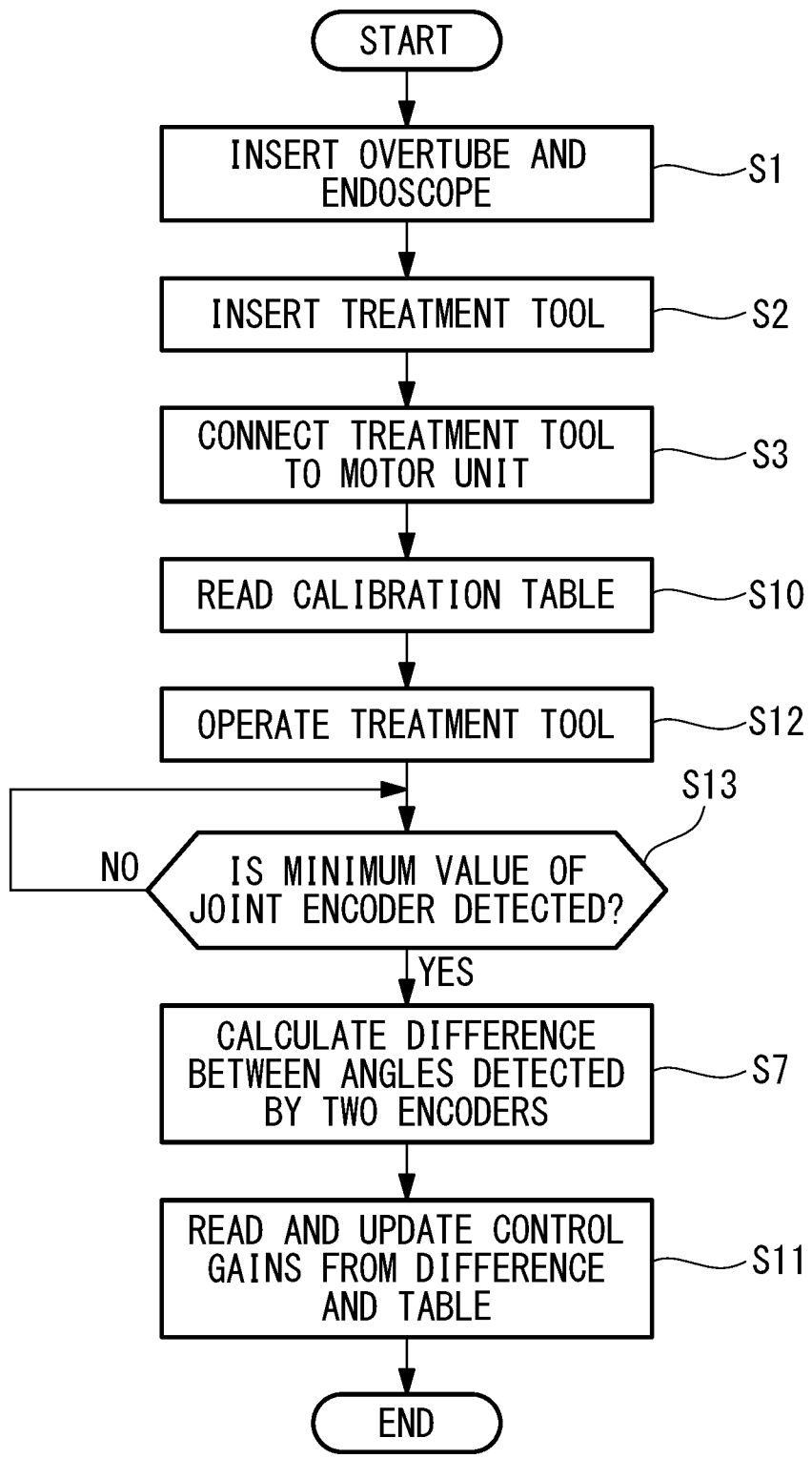
FIG. 10 is a flowchart showing a modification of the calibration procedure in FIG. 9.

In addition, although each of the above-described embodiments has been described by way of an example where the calibration mode and the operation mode are switched to each other, the user may adjust the transfer function while moving the joint 7 by operating the operation/input unit 4 without performing mode switching. As shown in, for example, FIG. 10, when the user operates the treatment tool 2 (step S12), the flow is suspended until the joint encoder 10 detects the minimum unit angle (step S13).

When the joint encoder 10 detects the minimum unit angle, the difference between the swivel angle of the joint 7 detected by the joint encoder 10 and the estimation angle based on the motor encoder 14 is promptly calculated (step S7), the control gains kd and ke are read out from the table, and the transfer function of the FF control unit 17 is updated (step S11). By doing so, the transfer function is updated properly while the user is operating the operation/input unit 4 without having to wait for a calibration motion.

Figure 11:
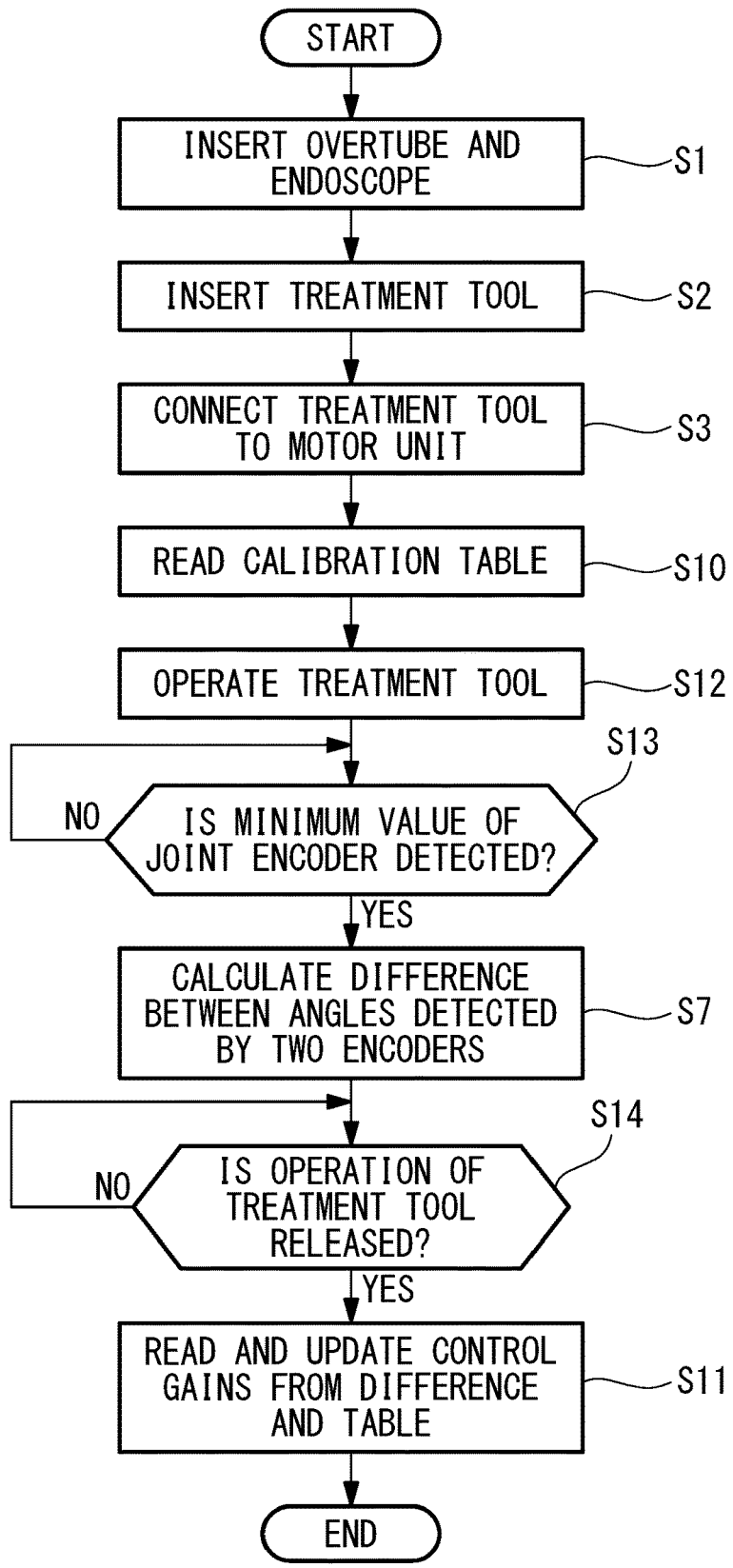
FIG. 11 is a flowchart showing another modification of the calibration procedure in FIG. 9.
Figure 12:
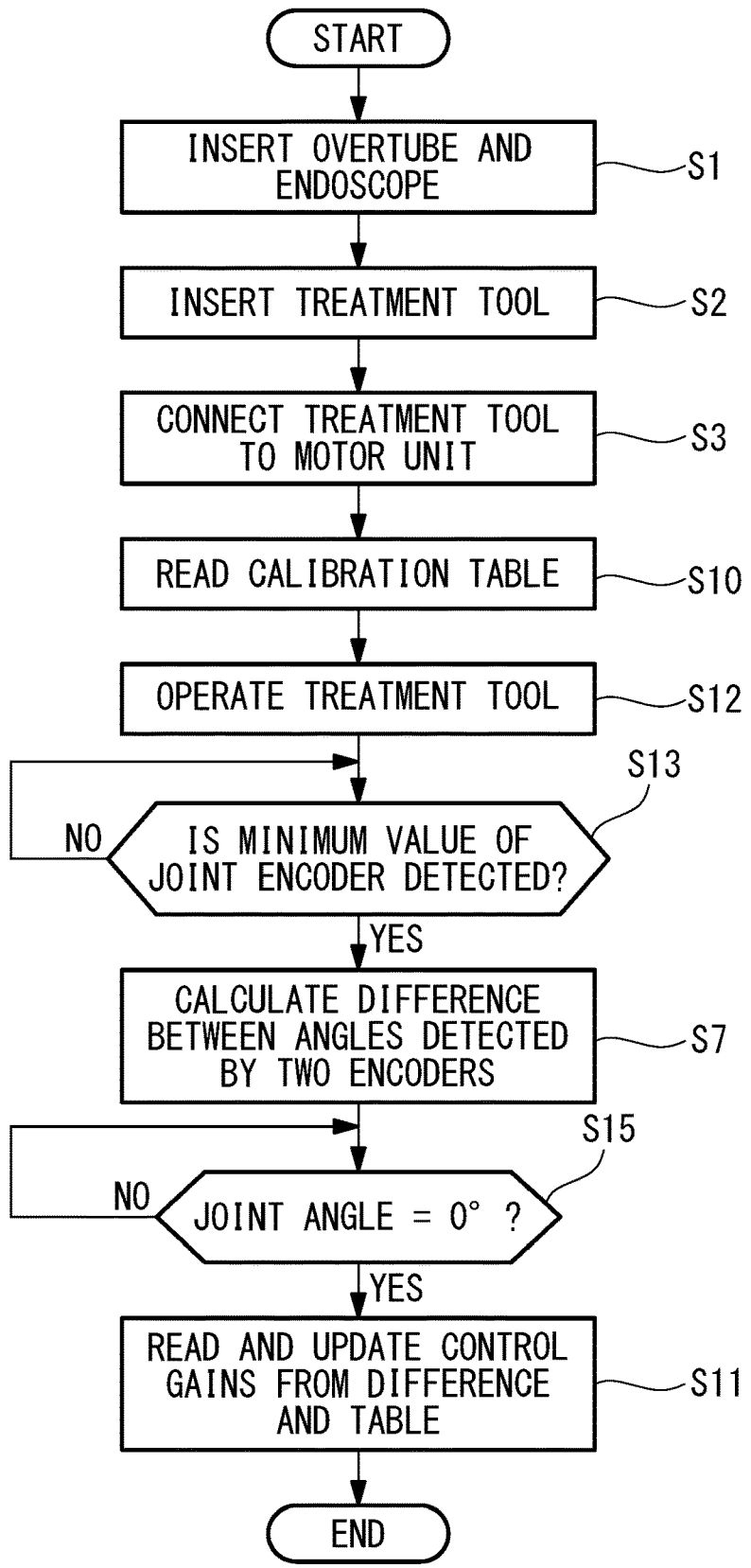
FIG. 12 is a flowchart showing still another modification of the calibration procedure in FIG. 9.

Furthermore, as shown in FIG. 11, in order to prevent the operational feeling from changing as a result of the transfer function being changed while the user is operating the operation/input unit 4, the present embodiment may be configured so that even after a difference used to read out the control gains kd and ke from the table has been calculated, the transfer function is not changed until a command for releasing the operation of the treatment tool is input on the input unit 16 (step S14). In other words, because the transfer function is updated while the operation of the treatment tool is released, it is possible to prevent the operational feeling from changing while the operation is being performed. Instead of this, as shown in FIG. 12, the present embodiment may be configured to wait until the angle of the joint 7 becomes 0° (step S15), so that the transfer function may be updated when the angle of the joint 7 becomes 0°.

Figure 13:
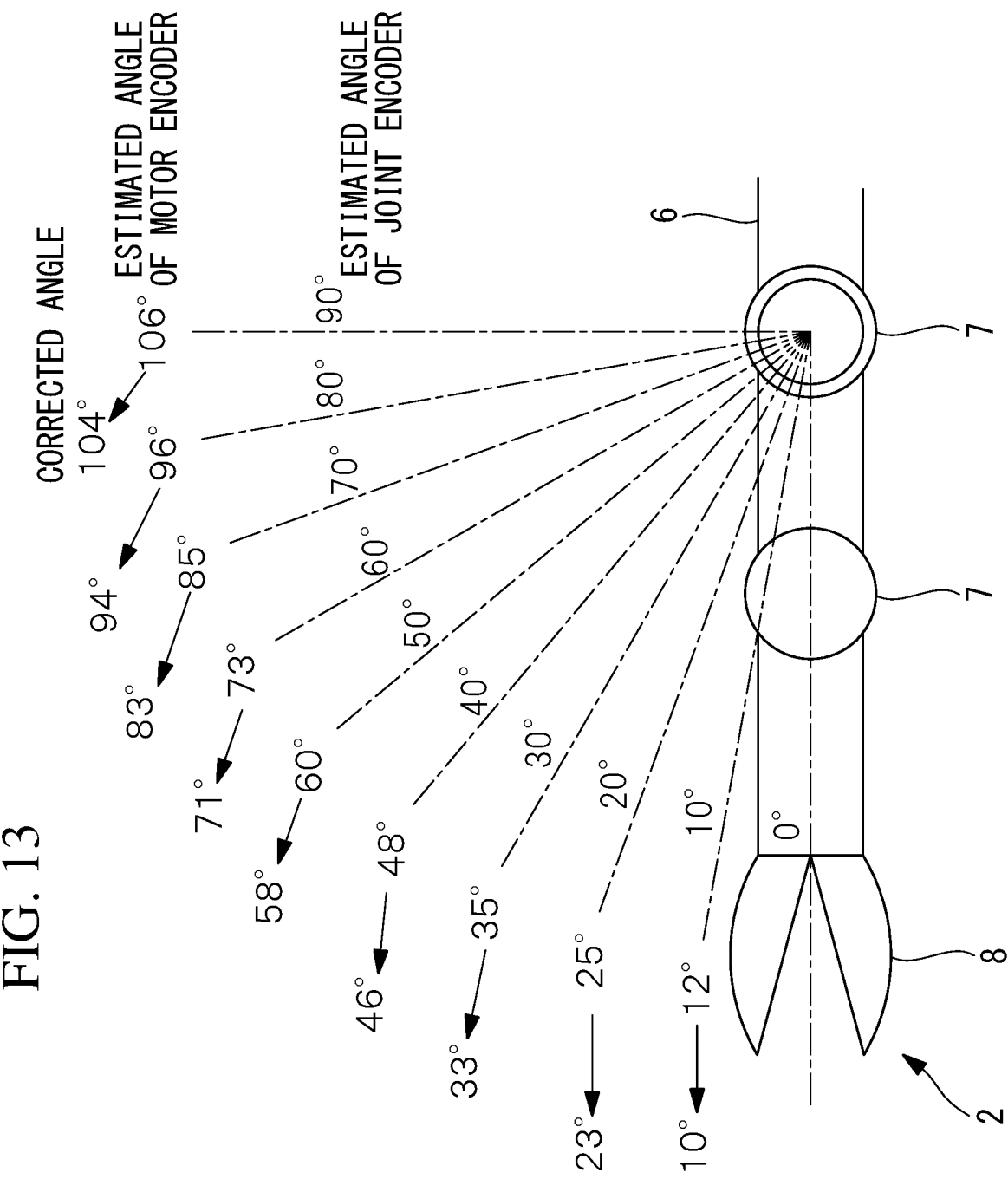
FIG. 13 is a diagram for illustrating a modification of the calibration motions in FIG. 4.

In addition, as shown in FIG. 13, as soon as the swivel angle of the joint 7 detected by the joint encoder 10 changes by the minimum unit angle (e.g., 10°), the ratio (e.g., $\theta 2/\theta 1=1.2$) between the swivel angle $\theta 1$ (e.g., 10°) of the joint 7 detected by the joint encoder 10 and the rotation angle $\theta 2$ (e.g., 12°) of the motor 13 detected by the motor encoder 14 may be calculated and stored as the control gain ke, so that subsequently, the control gain ke may be calculated and updated in the same manner each time the swivel angle changes by the minimum unit angle.

In addition, as soon as the swivel angle of the joint 7 detected by the joint encoder 10 changes by the minimum unit angle (e.g., 10°) after the joint 7 is made to swivel so as to turn back in the swiveling direction, the difference (e.g., 4°) between the estimation angle (e.g., 12°) of the motor encoder 14 calculated on the basis of the swivel angle (e.g., 10°) of the joint 7 detected by the joint encoder 10 and the control gain ke (e.g., 12°), and the rotation angle (e.g., 16°) detected by the motor encoder 14 may be calculated as the control gain kd, thus updating the control gain kd.

In addition, although this embodiment has been described by way of an example where the transfer-function adjusting unit 20 adjusts the transfer function of the FF control unit 17 in the controller 5, a transfer function of the motor control unit 18 may be adjusted. Furthermore, a sensor (not shown in the figure) for detecting the shape of the insertion section 6 of the endoscope may be provided, so that a calibration motion can be executed when a change in the shape of the insertion section 6 is detected by the sensor.

In addition, although a rotational joint is used as an example of the joint 7, the joint 7 may be applied to any other joint, such as a slide joint. Furthermore, although the rotationally driven motor 13 is used as an example of the actuator, instead of this, the motor 13 may be applied to any other actuator, such as a translationally driven motor or cylinder.

The above-described embodiment also leads to the following aspects. One aspect of the present embodiment is a medical manipulator system including: an elongated insertion section including a joint at a distal end portion; a first sensor for detecting an amount of motion of the joint of the insertion section; an actuator that is disposed at a proximal end of the insertion section and that operates to drive the joint via a wire; a second sensor for detecting an amount of operation of the actuator; an operation/input unit operated by a user; and a controller for generating a control signal to the actuator, wherein the controller includes an operation mode in which the control signal is generated via a transfer function that receives, as, inputs, an input value on the operation/input unit and the amount of operation of the actuator detected by the second sensor and a calibration mode in which the transfer function is adjusted on the basis of the amount of motion of the joint detected by the first sensor and the amount of operation of the actuator detected by the second sensor.

According to this aspect, when the user performs an operation or an input by operating the operation/input unit, the actuator is operated as a result of an operating command in accordance with the input value being input to the controller, and the driving force of the actuator is transmitted via the wire to the joint disposed at the distal end portion of the insertion section, thereby moving the joint. In the operation mode, a control signal is generated via the transfer function that receives as, inputs, an input value entered through an operation/input and the amount of operation of the actuator detected by the second sensor. At this time, the detected amount of operation of the actuator is fed back, and the amount of operation of the actuator is controlled so as to reduce the deviation with respect to the operating command in accordance with the input value.

In addition, in the calibration mode, the amount of motion of the joint is detected by the first sensor, and the transfer function is adjusted on the basis of the amount of motion detected by the first sensor and the amount of operation of the actuator detected by the second sensor. After the transfer function is adjusted, the actuator is controlled on the basis of an input value and the amount of operation detected by the second sensor, without relying on the amount of motion detected by the first sensor. By doing so, even when a compact, low-resolution encode is used as the first sensor, the joint at the distal end of the insertion section can be stably controlled as instructed with the operating command, irrespective of looseness and friction of the wire, thus making it possible to reduce the diameter of the distal end portion of the insertion section.

In the above-described aspect, when the joint is moved by a prescribed amount in the calibration mode, the transfer function may be adjusted so that the difference between the amount of motion detected by the first sensor and the amount of operation detected by the second sensor is equal to or smaller than a predetermined threshold value. By doing so, the transfer function is adjusted so that the amount of motion detected by the first sensor approaches the amount of operation detected by the second sensor when the joint is moved by the prescribed amount, thus making it possible to control the actuator in a highly accurate and stable manner on the basis of the amount of operation detected by the second sensor, without using the first sensor.

In addition, in the above-described aspect, when the joint is made to perform a predetermined reciprocating motion in the calibration mode, the transfer function may be adjusted so that the difference between the amount of motion detected by the first sensor and the amount of operation detected by the second sensor is equal to or smaller than a predetermined threshold value. By doing so, the difference between the amount of motion detected by the first sensor and the amount of operation detected by the second sensor, due to backlash and friction that are generated when the joint is made to perform a reciprocating motion, is reduced, thereby making it possible to stably control the actuator as instructed with an operating command.

In addition, in the above-described aspect, when the joint is made to perform a plurality of motions by a prescribed amount in the calibration mode, the transfer function may be adjusted so that the average value of the differences between the amounts of motion detected by the first sensor and the amounts of operation detected by the second sensor is equal to or smaller than a predetermined threshold value. By doing so, the differences between the amounts of motion detected by the first sensor and the amounts of operation detected by the second sensor, the differences fluctuating according to the moving position of the joint, are averaged, thus making it possible to control the actuator easily.

In addition, in the above-described aspect, the controller may further include a table for storing the difference and the transfer function adjusted with the difference such that the difference is associated with the adjusted transfer function, and the transfer function may be adjusted by using the table in the calibration mode. By doing so, it is possible to employ the transfer function that is stored in the table in association with the difference between the amount of motion detected by the first sensor and the amount of operation detected by the second sensor, thereby making processing simple.

REFERENCE SIGNS LIST

1 Medical manipulator system
4 Operation/input unit
5 Controller
6 Insertion section
7 Joint
10 Joint encoder (first sensor)
12 Wire
13 Motor (actuator)
14 Motor encoder (second sensor)

The invention claimed is:

1. A medical manipulator system comprising:
an elongated insertion section including a joint at a distal end portion of the insertion section;
a first sensor configured to detect an amount of rotational motion of the joint of the insertion section;
an actuator disposed at a proximal end of the insertion section, the actuator being configured to drive the joint via a wire connected to the joint;
a second sensor configured to detect an amount of operation of the actuator based on a rotation angle of the actuator;
an input device operated by a user; and
a controller configured to:
generate a control signal based on:
an operation mode in which the control signal is generated by a transfer function that receives, as inputs, an input target value of a rotation angle of the joint that is input on the input device and the amount of operation of the actuator detected by the second sensor, and
a calibration mode in which the transfer function is adjusted based on comparing a predetermined threshold value to a difference between: (i) the amount of rotational motion of the joint detected by the first sensor and (ii) the amount of operation of the actuator detected by the second sensor;
transmit the generated control signal to the actuator to drive the joint based on the generated control signal; and
repeat the calibration mode until the difference is equal to or smaller than the predetermined threshold value.

2. The medical manipulator system according to claim 1, wherein, when the joint moves by a predetermined amount in the calibration mode, the transfer function is adjusted so that the difference between the amount of rotational motion detected by the first sensor and the amount of operation detected by the second sensor is equal to or smaller than the predetermined threshold value.

3. The medical manipulator system according to claim 2, wherein:
the controller stores a table including a value of the difference and the transfer function adjusted by the value of the difference such that the difference is associated with the adjusted transfer function, and
the transfer function is adjusted by using the table in the calibration mode.

4. The medical manipulator system according to claim 1, wherein, when the joint performs a predetermined reciprocating motion in the calibration mode, the transfer function is adjusted so that the difference between the amount of rotational motion detected by the first sensor and the amount of operation detected by the second sensor is equal to or smaller than the predetermined threshold value.

5. The medical manipulator system according to claim 1, wherein, when the joint performs a predetermined plurality of motions in the calibration mode, the transfer function is adjusted so that an average value of differences between each of the amounts of rotational motion detected by the first sensor and each of the amounts of operation detected by the second sensor is equal to or smaller than the predetermined threshold value.

6. A method for operating a medical manipulator system that includes a first sensor configured to detect an amount of rotational motion of a joint provided at a distal end portion of an elongated insertion section, a second sensor configured to detect an amount of operation of an actuator based on a rotation angle of the actuator disposed at a proximal end of the insertion section and drive the joint via a wire connected to the joint, and an input device operated by a user, the method comprising;
setting control gains of a transfer function to initial values, the transfer function receiving, as inputs, an input target value of a rotation angle of the joint that is input on the input device and the amount of operation of the actuator detected by the second sensor;
moving the joint with a predetermined pattern;
calculating a difference between the amount of rotational motion of the joint detected by the first sensor and the amount of operation of the actuator detected by the second sensor;
determining whether the calculated difference is equal to or less than a predetermined threshold value;
in response to determining that the calculated difference is not equal to or less than the predetermined threshold value, updating the control gains of the transfer function;
generating and transmitting a control signal based on the transfer function to the actuator to drive the joint based on the generated control signal; and
repeating updating the control gains of the transfer function until the calculated difference is equal to or smaller than the predetermined threshold value.

* * * * *